United States Patent [19]

Adell

[11] Patent Number: 5,406,962
[45] Date of Patent: Apr. 18, 1995

[54] DENTAL ARCH APPLIANCES

[75] Inventor: Loren S. Adell, 200 Adell Blvd., Sunnyvale, Tex. 75182

[73] Assignees: Loren S. Adell; Michael Adell, both of Sunnyvale, Tex.

[21] Appl. No.: 801,673

[22] Filed: Dec. 2, 1991

[51] Int. Cl.[6] .................................. A61C 5/14
[52] U.S. Cl. .................... 128/859; 128/861
[58] Field of Search ............... 128/859–862, 128/62 A; 2/2; 433/34, 33

[56] References Cited

U.S. PATENT DOCUMENTS

| 2,833,278 | 5/1958 | Ross ............................. 128/862 |
| 3,124,129 | 3/1964 | Grossberg ....................... 128/862 |
| 3,303,844 | 2/1967 | Johnson ......................... 128/862 |
| 3,943,924 | 3/1976 | Kallestad ........................ 128/861 |
| 4,765,324 | 8/1988 | Lake ............................. 128/861 |
| 4,955,393 | 9/1990 | Adell ............................ 128/859 |
| 5,003,994 | 4/1991 | Cook ............................ 128/859 |
| 5,031,638 | 7/1991 | Castaldi ......................... 128/861 |
| 5,103,838 | 4/1992 | Yousif ........................... 128/861 |

Primary Examiner—Michael A. Brown
Attorney, Agent, or Firm—George L. Boller

[57] ABSTRACT

An intra-oral appliance that is associated with a pair of dental arches having a trough for receiving an upper dental arch. A second layer in a covering relation to the first layer opposite the trough, the second layer being relatively harder than the first layer. A third layer in covering relation to the second layer opposite the first layer. The third layer is relatively harder that the second layer.

12 Claims, 10 Drawing Sheets

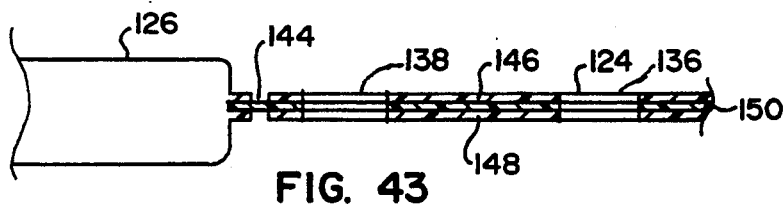
FIG. 43
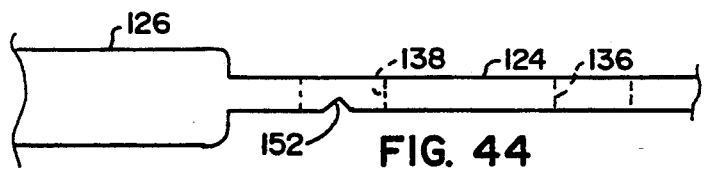
FIG. 44
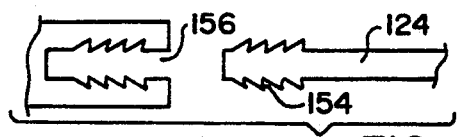
FIG. 45
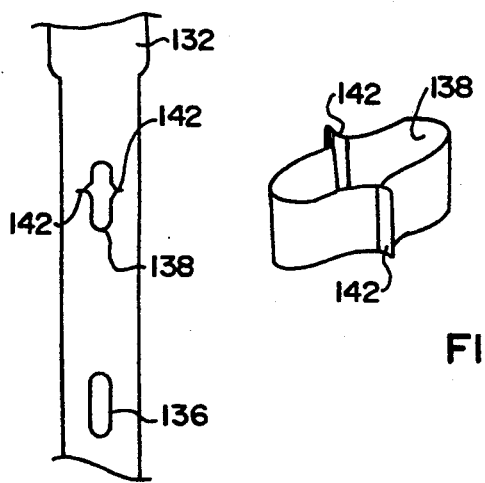
FIG. 41
FIG. 42
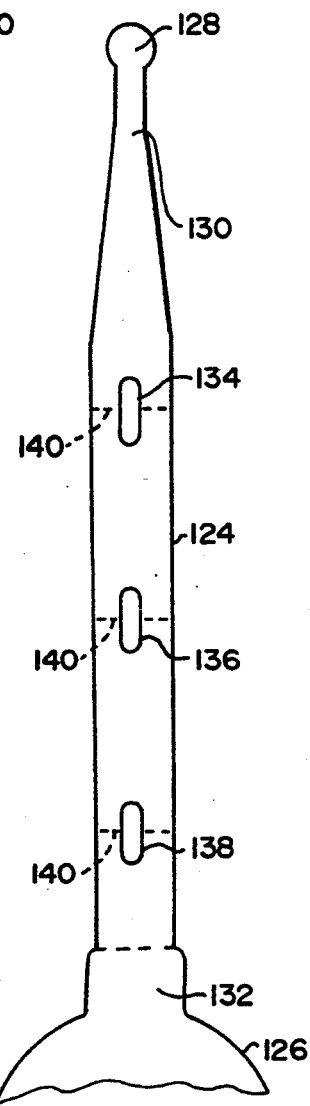
FIG. 40
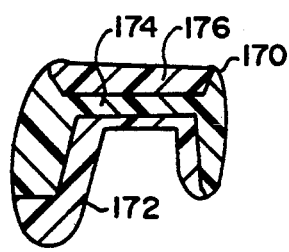
FIG. 51

— 1 —

DENTAL ARCH APPLIANCES

FIELD OF THE INVENTION

This invention relates to appliances that are used in association with dental arches, such as mouthguards, splints, and impression trays.

BACKGROUND AND SUMMARY OF THE INVENTION

The improvements that are the subject of this patent application are the result of Applicant's continuing work on inventions disclosed in previous patent applications in his name. Applicant's issued patents are: U.S. Pat. No. 4,955,393 dated Sep. 11, 1990; and U.S. Pat. No. 4,983,334 dated Jan. 8, 1991. Pending applications are: U.S. Pat. No. 07/469,286 filed Jan. 24, 1990 now U.S. Pat. No. 5,082,007; and U.S. Pat. No. 07/780,545 filed Oct. 22, 1991, which has the benefit of U.S. Pat. No. 07/616,329 filed Nov. 21, 1990 and of U.S. Pat. No. 07/329,407 filed Mar. 27, 1989 all of these three applications now being abandoned.

The references cited in those applications constitute art that is known to Applicant, and a recently issued patent on the subject of mouthguards is U.S. Pat. No. 5,031,638 issued Jul. 16, 1991.

In Applicant's prior patent applications on the subject matter hereof, new and unique multi-layer (multi-laminar) mouthguard constructions are disclosed. Such multi-layer constructions provide significant improvement in mouthguard performance and features. In one aspect, the present invention relates to further improvements in multi-layer mouthguards, both as to the multi-layer structure thereof and to methods for making them. In another aspect, the invention relates to new and unique molding methods for fabricating mouthguards, particularly to: supporting a main body of a mouthguard within a cavity of a mold while a liner is molded onto the main body; and building up a multi-layer mouthguard one layer at a time by a process that the Applicant refers to as "pyramid molding". A further aspect of the invention relates to mouthguards that have an attaching strap for attachment, or tethering, to an article worn by the user of the mouthguard. Such an article may be a sports headgear, i.e. the face mask or face bar of a football helmet for example. A still further aspect of the invention relates to a lip protector that fits onto such an attaching strap and over the lips of the user.

Principles of the invention are not necessarily limited to a mouthguard as that word is commonly understood. Principles are applicable to intra-oral appliances associated with at least one dental arch, including impression trays for taking an impression of a dental arch and orthodontic splints.

Further aspects of the invention, along with other features, advantages and benefits will be seen in the ensuing description and claims which are accompanied by drawings. The drawings describe a presently preferred embodiment of the invention according to the best mode contemplated at the present time for carrying out the invention.

BRIEF DESCRIPTION OF THE DRAWINGS

FIG. 40 is a plan view of an attaching strap extending from a mouthguard.

FIG. 41 is a fragmentary view of a portion of the strap including a modification in accordance with the invention.

FIG. 42 is a fragmentary perspective view of a portion of FIG. 41.

FIG. 43 is a longitudinal cross sectional view through another embodiment of attaching strap.

FIGS. 44–45 are fragmentary elevational views of other embodiments of attaching straps.

FIG. 51 is a transverse cross section of a splint.

DESCRIPTION OF THE PREFERRED EMBODIMENT

Figure 1:
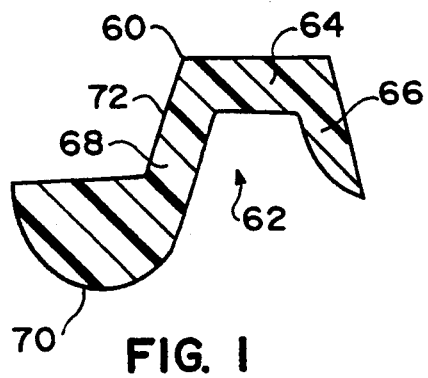
FIG. 1 is a transverse cross sectional view through a first layer of a mouthguard.
Figure 2:
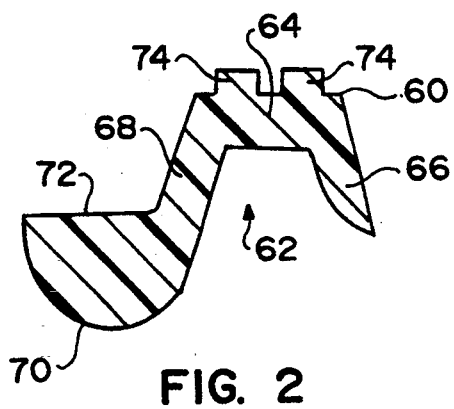
FIG. 2 is a transverse cross sectional view through a first layer of another embodiment of mouthguard.
Figure 3:
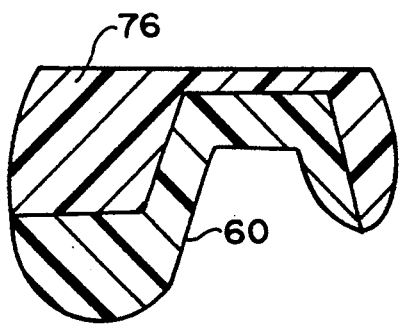
FIGS. 3–12 are respective transverse cross sectional views through ten different embodiments of mouthguard showing different second layers in association with the first layer of FIG. 1.
Figure 4:
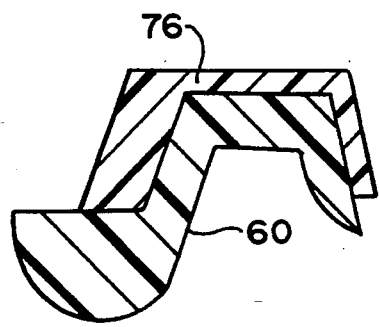
Figure 5:
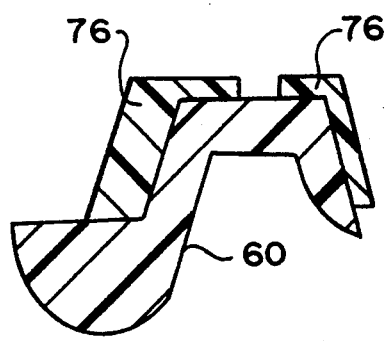
Figure 6:
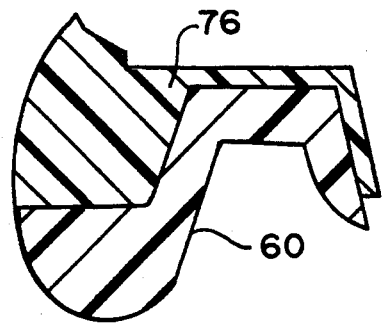
Figure 7:
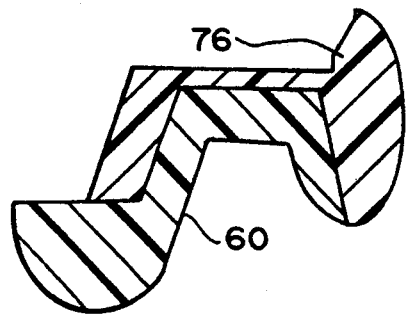
Figure 8:
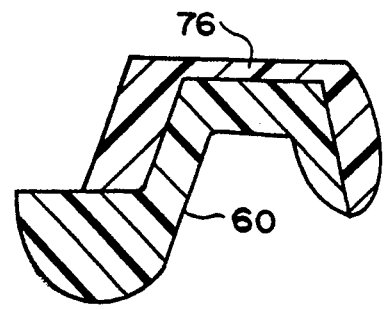
Figure 9:
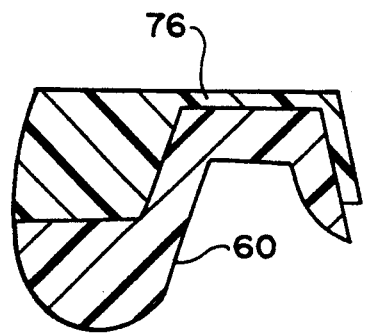
Figure 10:
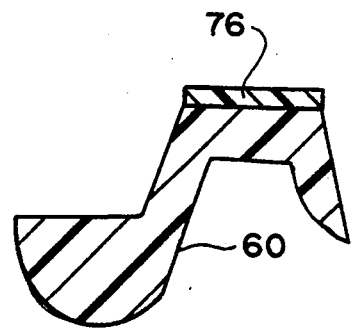
Figure 11:
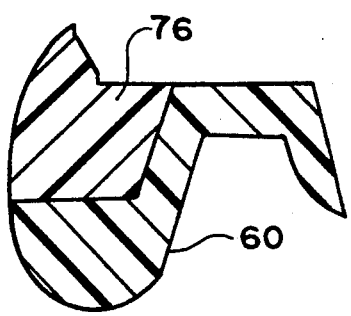
Figure 12:
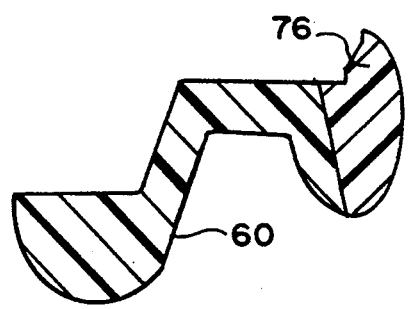
Figure 13:
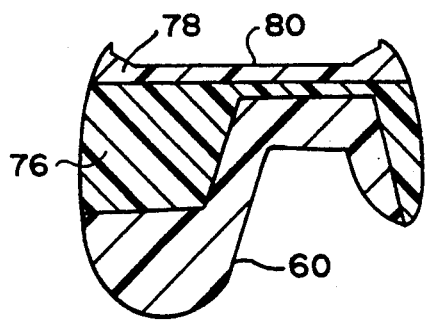
FIGS. 13–22 are respective transverse cross sectional views through the embodiments of FIGS. 3–12 respectively showing the addition of respective third layers.
Figure 14:
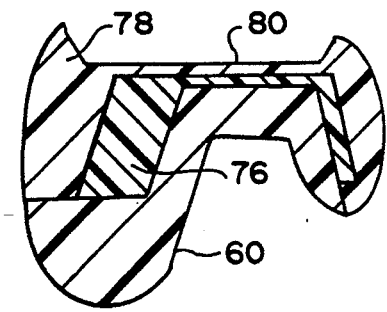
Figure 15:
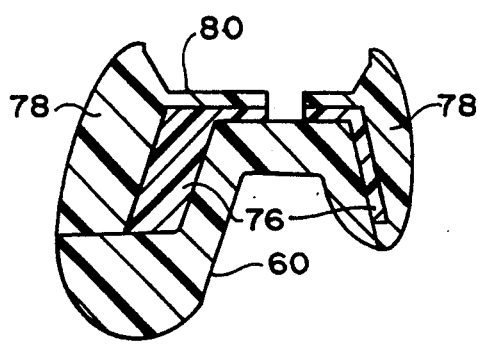
Figure 16:
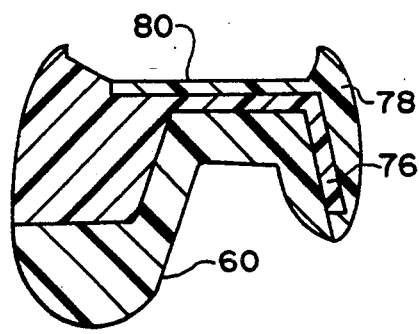
Figure 17:
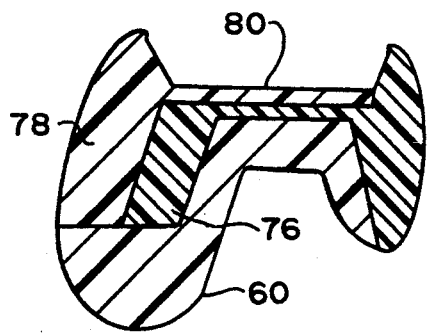
Figure 18:
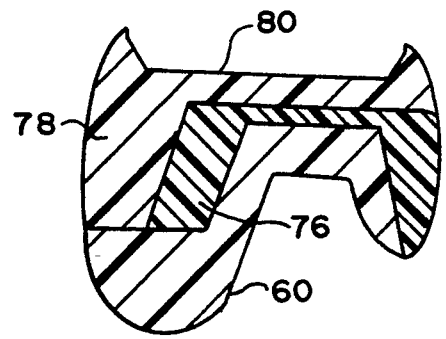
Figure 19:
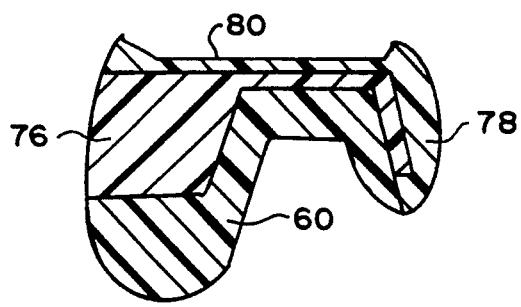
Figure 20:
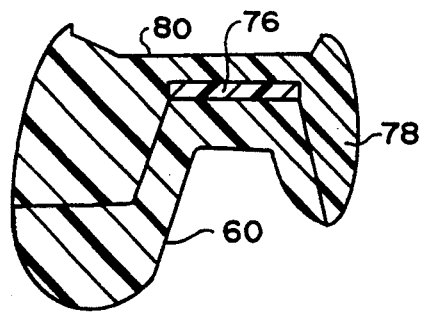
Figure 21:
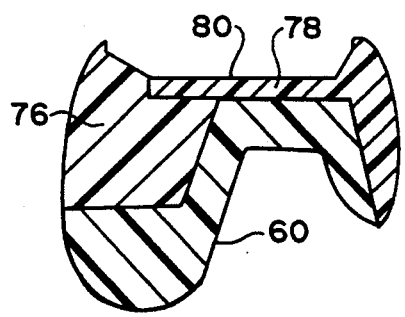
Figure 22:
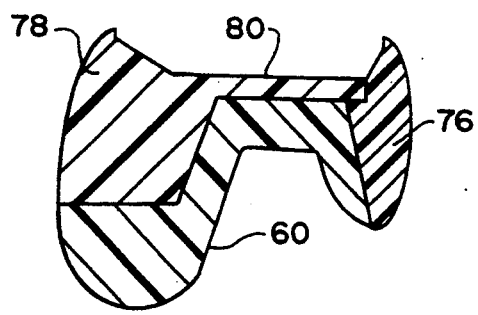

FIGS. 1 and 2 illustrate two examples of a first layer 60 for a mouthguard. Layer 60 is fabricated by molding a suitable molding material into the illustrated cross sectional shape. Preferably such molding is conducted in the cavity of a mold shaped to provide the general U-shape that is characteristic of a mouthguard. The preferred molding procedure is one in which the flowable material, for example ethylene vinyl acetate (EVA), is injected under pressure into the cavity and allowed to cure. Layer 60 forms that portion of the mouthguard that is associated with the upper dental arch. It comprises a trough 62 defined by an occlusal wall 64, a lingual wall 66, and a labial wall 68. The tip end of the labial wall is rounded at 70, and the labial wall also contains a large groove 72 as shown. The only difference between the embodiments of FIGS. 1 and 2 is that in FIG. 2 the surface of occlusal wall 64 contains two spaced apart ridges 74 opposite trough 62.

FIGS. 3–12 illustrate ten different embodiments having a second layer 76 united with the FIG. 1 embodiment of first layer 60. Each of the second layers is fabricated by molding a suitable molding material into the illustrated cross sectional shape. A portion of the mold in which the first layer 60 was fabricated may be used to retain the first layer and be cooperatively associated with further mold structure to cooperatively define a further mold cavity having a portion that is not occupied by first layer 60 so as to define a volume having the shape of the second layer 76. Flowable material is injected into this further mold cavity and allowed to cure to form the second layer 76 united to layer 60. Such unison may be obtained by the method described in the above-referenced application Ser. No. 07/780,545 wherein the second layer directly bonds to the first layer. The second layer is preferably a material which is somewhat harder (higher durometer) than layer 60. It may for example be a higher durometer EVA. In all embodiments of FIGS. 3–12, the second layer 76 is united to a surface of first layer 60 that is opposite trough 62. In the embodiments of FIGS. 3–9, the second layer 76 covers walls 64, 66, and 68; in FIG. 10, only wall 64; in FIG. 11, only wall 68; and in FIG. 12, only wall 66. Alternatively, it would be possible to carry out the molding of the second layer without the use of a part of the mold that was used to fabricate the first layer, but this would require that the first layer be removed from the mold in which it was fabricated and placed in a portion of the cavity of the second mold, rather than being retained in a portion of the mold in which it was molded and which is also used for cooperative association with the further mold structure used to fabricate the second layer 76.

Figure 23:
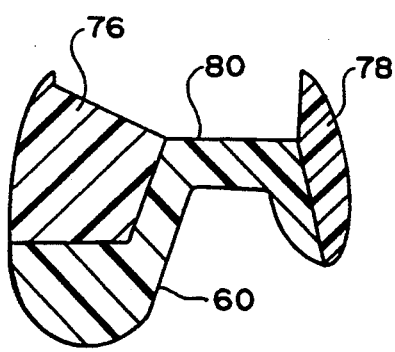
FIG. 23 is a view like that of FIG. 22, but with a different form of third layer.
Figure 24:
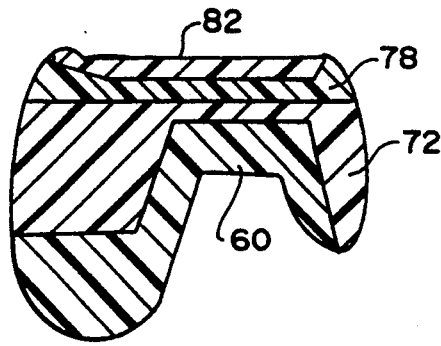
FIGS. 24–34 are respective transverse cross sectional views through the embodiments of FIGS. 13–23 respectively showing the addition of respective fourth layers.
Figure 25:
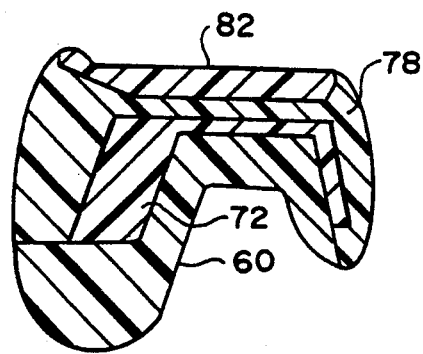
Figure 26:
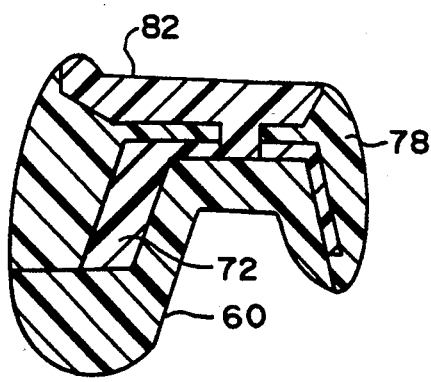
Figure 27:
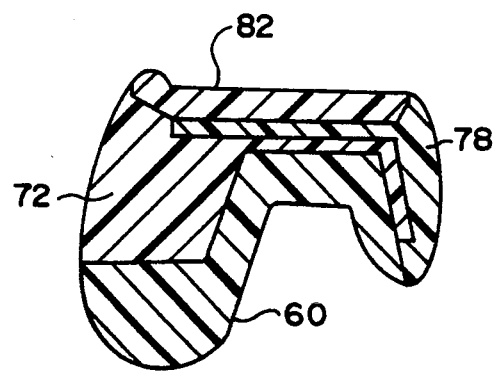
Figure 28:
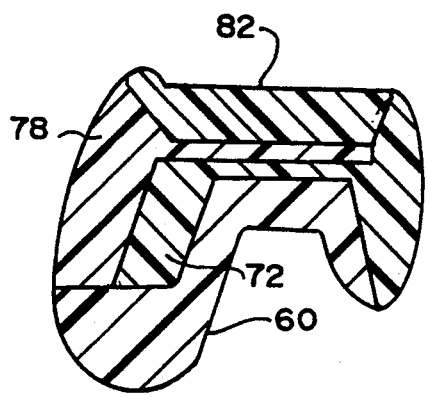
Figure 29:
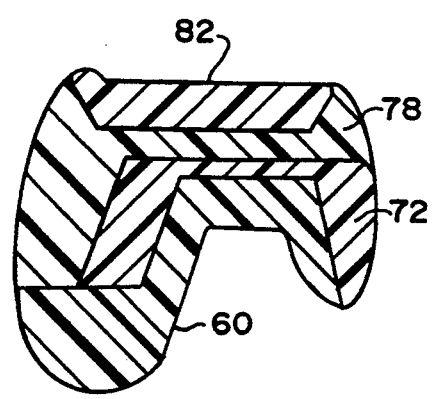
Figure 30:
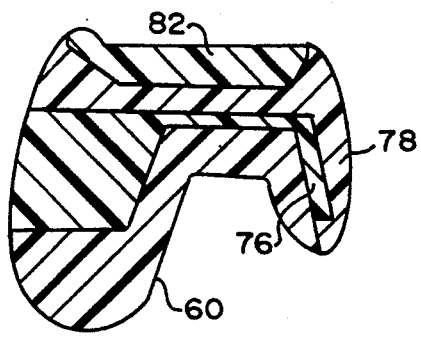
Figure 31:
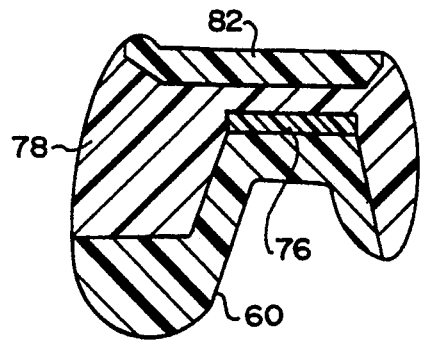
Figure 32:
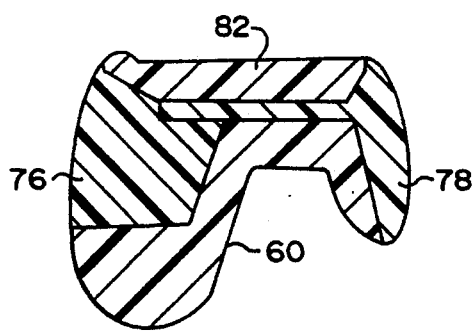
Figure 33:
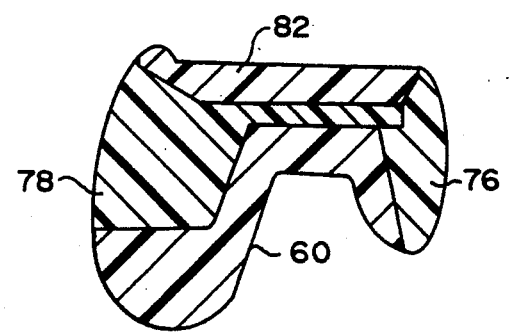
Figure 34:
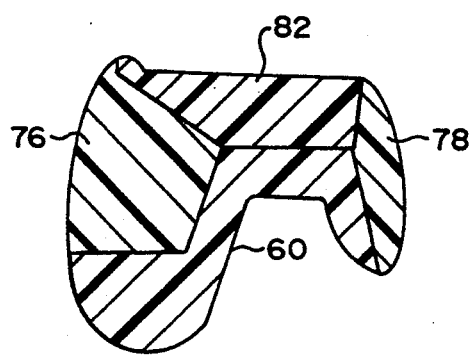

FIGS. 13–22 illustrate the ten embodiments of FIGS. 3–12 having received a third layer 78. The molding of the third layer is conducted in analogous fashion to the molding of the second layer. The united first and second layers are retained in a portion of the mold used to create the first layer, which is then cooperatively associated with a still further mold structure to cooperatively define a still further cavity having a portion that is not occupied by the first and second layers so as to define a volume having the shape of the third layer. Suitable molding material is flowed into the unoccupied volume and allowed to cure so as to unite the third layer with the previously united first and second layers, and thereby form the shapes as shown in FIGS. 13–22. Preferably the material of the third layer has a higher durometer than that of the second layer, and for example a suitable material may be a higher durometer EVA. As was done in fabricating the second layer, the third layer may be directly molded to the underlying layer(s) covered thereby. As can be seen from the various drawing FIGS., the third layer is in some instances applied only to the first layer, in other instances only to the second layer, and in still other instances to both the first and second layers. FIG. 23 is the only instance illustrated where the third layer is applied to only the first layer, and in this embodiment the second and third layers are used to provide the mouthguard with different durometer labial and lingual wall portions. In all embodiments of FIGS. 13–23, there is a shallow trough 80 provided opposite trough. 62.

The finished transverse cross sectional shape for the eleven embodiments of mouthguards represented by FIGS. 24–34 comprises a layer of material 82 in each trough 80. Layer 82 is the fourth layer and is fabricated in the same manner as the second and third layers. The united first, second, and third layers are retained in a portion of the mold used to fabricate the first layer, and they are then cooperatively associated with yet another mold structure to cooperatively define yet another mold cavity having a portion that is not occupied by the first, second, or third layers so as to define a volume having the shape of the fourth layer. Suitable molding material, which once again may be EVA, is flowed into this volume and allowed to cure so as to unite with the previously united first, second, and third layers. Preferably the fourth layer has a lower durometer than the second and third layers. Trough 80 and layer 82 are intended to receive the lower dental arch of the user. As can be seen in FIGS. 24–34, layer 82 covers only the third layer in some instances, only the second and third layers in others, and in the embodiment of FIG. 26, it unites with all three layers.

Figure 35:
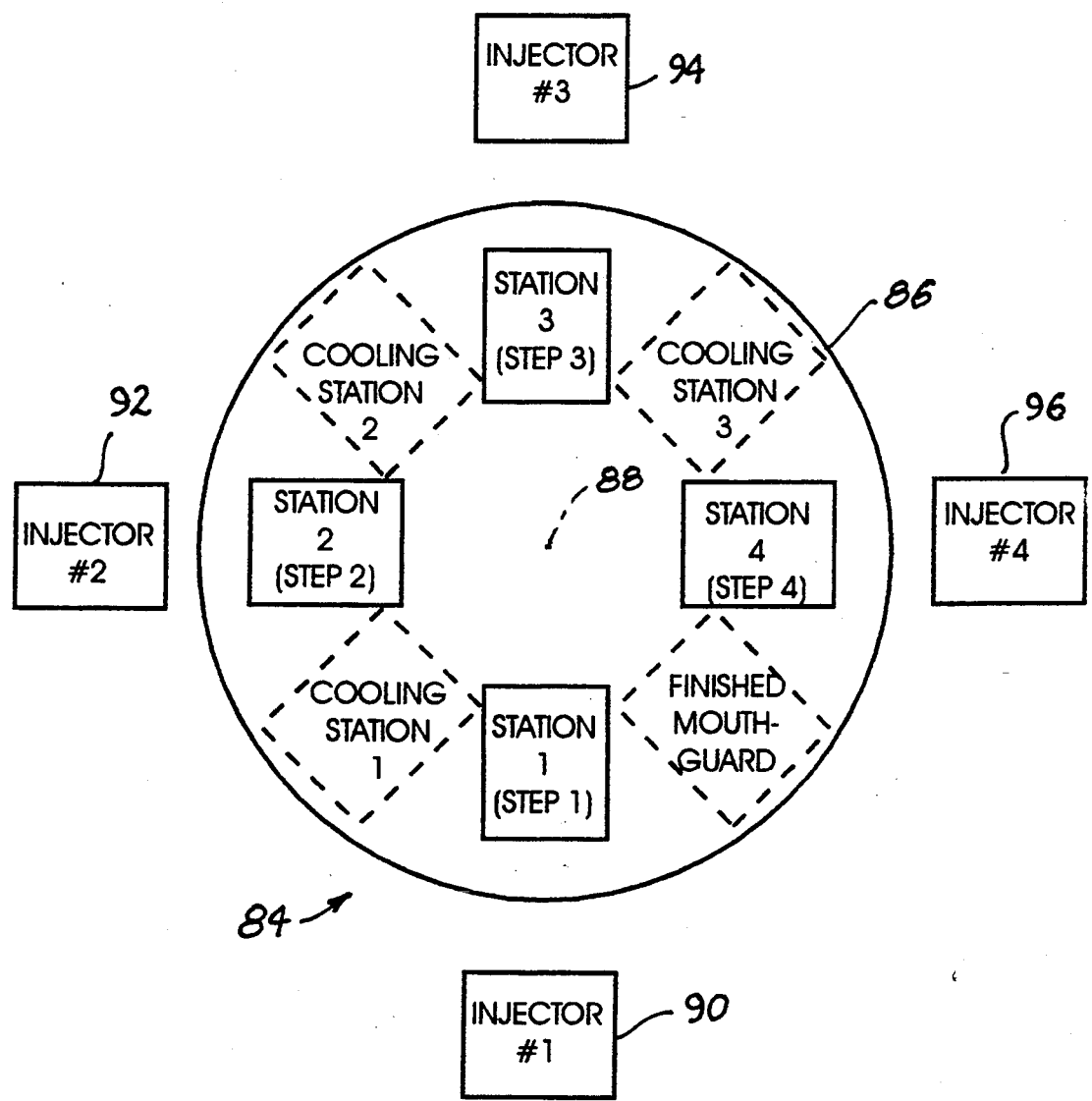
FIG. 35 is a plan view of a somewhat schematic nature illustrating a molding apparatus for making the mouthguards represented by FIGS. 1–34.

FIG. 35 depicts a molding apparatus 84 at which the four-layer mouthguards are fabricated. The apparatus comprises a rotary table 86 that can be indexed about an axis of rotation 88. Four injectors 90, 92, 94, and 96 are stationarily arranged at ninety degree increments around the perimeter of table 86. The mold that is used to fabricate the first layer 60 is at station #1 where it is associated with injector 90; the mold that is used to fabricate the second layer 76 is at station #2 where it is associated with injector 92; the mold that is used to fabricate the third layer 78 is at station #3 where it is associated with injector 94; and the mold that is used to fabricate the fourth layer 82 is at station #4 where it is associated with injector 96. Thus the first layer of a first mouthguard, the second layer of a second mouthguard, the third layer of a third mouthguard, and the fourth layer of a fourth mouthguard are simultaneously fabricated. Thereafter the table is indexed clockwise forty-five degrees to place each mouthguard-in-process at a cooling station where the previously injected layer is allowed to at least partially cure. The cooling station immediately after the fourth injection station is the one at which the finished mouthguard is removed.

At each station, the mold that contains the mouthguard-in-process is associated with the corresponding injector for introducing molding material into the mold cavity. After the material has been injected, the injector is disconnected from the mold and the table is indexed, first to the cooling stations and then to the next injection station. As explained earlier, a mouthguard-in-process on the table is carried by a portion of the mold used to make the first layer. This portion constitutes a carrier for the mouthguard-in-process that is indexed from injector to injector by the table. At each molding station this carrier is cooperatively associated with particular mold structure unique to that station for creating the particular layer that is to be molded at that station. Thus, the particular mold structure unique to each station remains at that station and does not index with the table. To the extent that molding material is introduced into a cavity via the carrier, it is necessary for the injector to be disconnected after 6he injection, as mentioned above. However, to the extent that material is introduced into a cavity through the particular mold structure that remains at a station, then the injector does not necessarily have to be disconnected from that structure. At each cooling station, it is possible that cooling equipment could be connected to a carrier upon arrival and disconnected before departure.

FIGS. 36–39 relate to an embodiment of mouthguard which comprises a main body 90' onto which liner material 92' is molded. The mouthguard has a general U-shape comprising an upper trough 94' for an upper dental arch and a lower trough 96' for a lower dental arch. Liner material lines both troughs, and the occlusal wall 98 of the main body 90' may comprise a series of holes 100 that provide for the upper and lower liners to be integrally joined.

Figure 38:
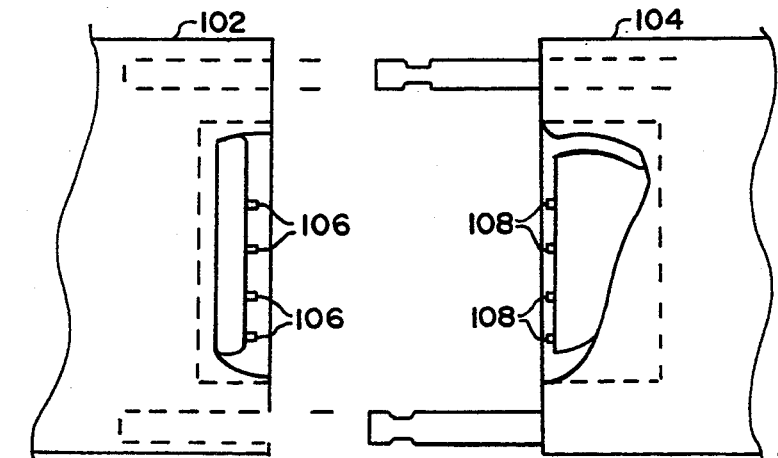
FIG. 38 is a fragmentary side elevational view of a mold for making the mouthguard of FIGS. 36 and 37.

Main body 90' is a material such as EVA, and therefore when it is placed into a mold cavity for the purpose of injection molding liner material onto it, it must be properly located and supported therein. It has been discovered that suitable support can be obtained by providing the mold cavity with a series of small stand-off pins that engage the occlusal wall of the main body and with wall-engaging members that engage lingual and labial walls of the main body. Such features may be used individually or jointly in any given mold. FIG. 38 shows a mold comprising separable mold members in separated condition and designated 102, 104 respectively. When they are operated closed to support a main body 90' within the cavity which they cooperatively define, a series of stand-off pins 106 engage the lower surface of occlusal wall 98 while a series of stand-off pins 108 engage the upper surface of the occlusal wall. The stand-off pins are arranged in a pattern around the main body as can be appreciated from consideration of FIG. 36 which shows a resulting pattern of small holes 110 that appear in the liner portions covering occlusal wall 98 after the liner has been injected into the cavity. The injection of the liner material into the cavity fills a volume that is unoccupied by the main body and defines the shape for the liner. The injected liner material covers the occlusal wall except at the locations where the occlusal wall surface is engaged by the stand-off pins. The holes 110 extend through the liner to the main body, but they have no significant effect on the mouthguard because they are much smaller in transverse cross section than any tooth of an arch with which the finished mouthguard is intended to be used.

Figure 39:
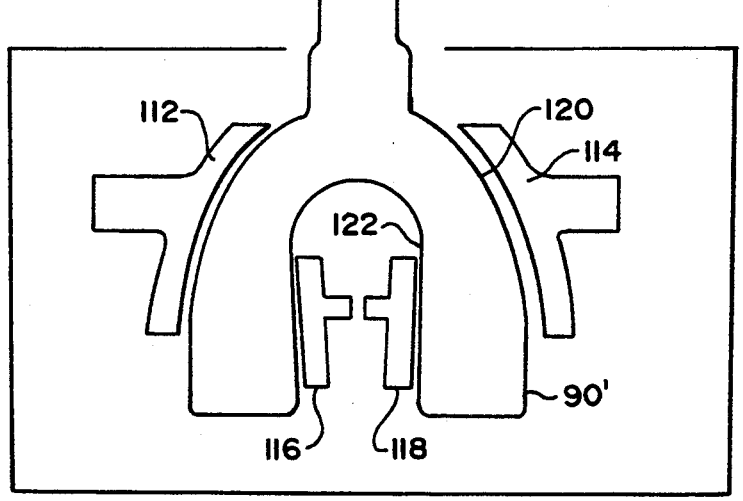
FIG. 39 is a side elevational view of a portion of a mold for making a mouthguard like that of FIG. 36.
Figure 46:
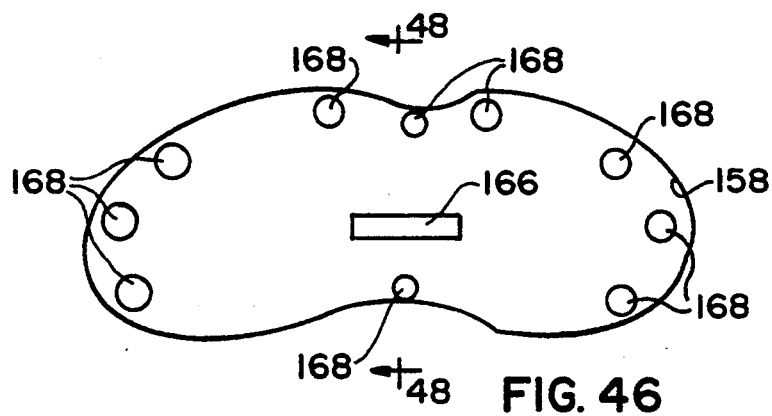
FIG. 46 is a front elevational view of a lip guard in accordance with the invention.
Figure 49:
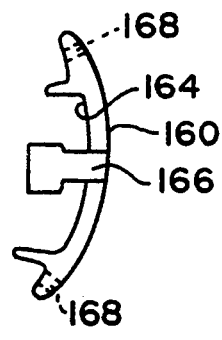
FIG. 49 is a view of one of the parts of FIG. 48 by itself.
Figure 48:
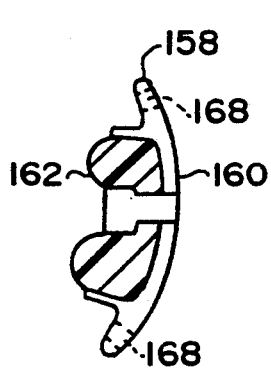
FIG. 48 is a cross sectional view in the direction of arrows 48—48 in FIG. 46.
Figure 47:
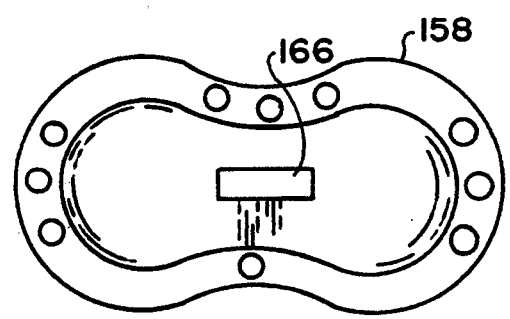
FIG. 47 is a rear view of FIG. 46.
Figure 50:
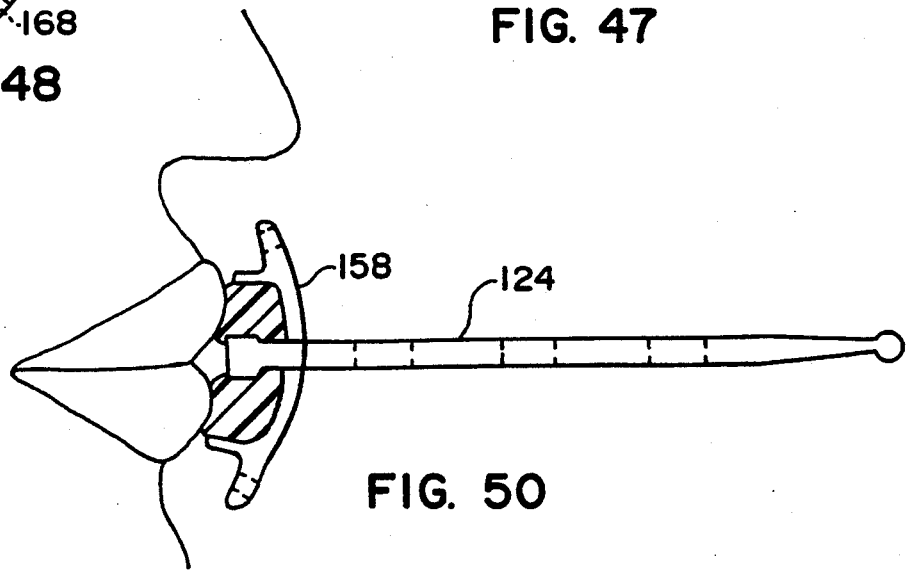
FIG. 50 is a view like FIG. 48 illustrating usage.

FIG. 39 depicts the mold to comprise a first set of wall-engaging members 112, 114 and a second set of wall-engaging members 116, 118. The members 112, 114 are arranged in opposition for movement toward each other to grip the labial wall 120 of the main body while members 116, 118 are arranged for movement away from each other to grip the lingual wall 122 of the main body. Members 112, 114 have concave faces contoured to match the convex shapes of the portions of the labial wall engaged thereby. When a main body is loaded into the open mold members, the members 112, 114 are retracted, as are members 116, 118. The members 112, 114 are advanced to grip the main body and the members 116, 118 are also advanced to grip it. The motions for operating the members may be generated by cam mechanisms that couple the motion of the closing mold members to the members 112, 114, 116, 118. Members 112, 114 have a mesio-distal extent that is greater than that of members 116, 118. Alternatively to the use of cam mechanisms for operating the members 112, 114, 116, 118, as described, they may be operated by powered slides, cylinder actuated slides for example.

A still further feature of the invention relates to an attaching, or tethering, strap that is sometimes used with sports mouthguards. FIG. 40 shows such a strap 124 extending from the mesial region of the U-shaped mouthguard 126. The free end of strap 124 comprises a ball tip 128 at the end of a taper 130. The strap has uniform thickness throughout its length to point of merger with a protuberance 132 of the U-shaped mouthguard. The strap also has several elongated through-holes 134, 136, 138. Tethering of the mouthguard to a sports helmet facebar for example is accomplished by looping the far end of the strap around the bar and snapping the ball tip 128 through a selected one of the holes 134, 136, 138. Between the taper 130 and the protuberance 132, strap 124 has a uniform width. Accordingly, the application of a tensile force along the length of the strap will tend to ultimately sever the strap at one of the regions designated 140 if the tensile force becomes sufficiently large. This is because the locations of the holes are the weakest locations along the length of the strap. When a tethered mouthguard is in use, relative movement of the point of tethering away from the U-shaped mouthguard in the user's mouth will generate tensile force in the strap. The Applicant has discovered that a break-away feature in the strap may be useful when the tensile force exceeds a certain magnitude. FIGS. 41-45 illustrate several embodiments for such a break-away feature.

FIGS. 41 and 42 show the incorporation of the feature by providing slits 142 on opposite sides of the elongated through-hole 140 nearest protuberance 132. The slits are short but provide a certain weakening that will cause the strap to break across hole 138 in response to the application of a predetermined magnitude of tensile force to be strap between the point of tethering and the mouthguard.

FIG. 43 shows a weakening 144 that will provide the break-away feature. The strap in this embodiment is of multi-layer construction, such construction per se being believed broadly new in a mouthguard tethering strap, and comprises transverse discontinuities in upper and lower layers 146, 148 adjacent the mouthguard. The strap has a central layer 150 between the layers 146, 148. Each of the layers 146, 148, 150 can be molded integrally with a corresponding layer of the mouthguard.

FIG. 44 shows a line of weakening 152 that provides the break-away feature in the form of a V-notch extending transversely across the strap in one surface thereof. This V-notch can be molded into the strap.

FIG. 45 depicts the break-away feature as a barbed end 154 of the strap that is inserted into a complementary barbed socket 156 in the mouthguard. Such socket may be in a protuberance such as 132, or it may be formed in the relatively harder main body 90 if the protuberance 132 is formed in relatively less rigid material such as that lining the main body.

FIGS. 46-50 relate to a further aspect of the invention, namely a lip protector 158 that fits onto a tethering strap of a mouthguard. Lip protector 158 is fabricated by multi-layer molding. It comprises a main body 160 of relatively harder material and a liner 162 of relatively softer material. Main body 160 has a generally concave shape for conformance with the lips and surrounding area. The rear face contains a cavity 164 that contains liner 162. A through-hole 166 extends centrally through both main body and liner to allow the lip guard to fit onto a strap 124 in the manner of FIG. 50. In that Figure it can be seen that the liner protrudes rearwardly for contacting the lips. In the perimeter of the main body 160 there are several airholes 168.

FIG. 51 shows the transverse section of a U-shape device in the form of a splint 170. Splint 170 is fabricated according to the method described above, but comprises only three layers 172, 174, 176. Layer 174 constitutes the main body which has troughs on opposite sides. Layer 172 is softer than layer 174 and lines the trough that receives the upper dental arch. Layer 176 is harder than the layer 174 and fills the trough that is associated with the lower dental arch. Layer 172 provides for the impression of an exact impression of the upper arch. The surface of layer 176 is flat and sufficiently hard that the teeth of the lower arch can move over it. Thus the device of FIG. 51 is a splint that is useful in the treatment of TMJ disorders.

Principles of the invention can be applied to various intra-oral appliances, and are not necessarily limited to mouthguards as that word is commonly understood by the general public. For example, the device of FIG. 51 just described may have the appearance of a mouthguard, but it is intended to function as a splint because of the specific nature of its troughs and the material of the liners thereof. In the case of what is commonly understood as a mouthguard, the layers disposed in the troughs are tooth-impressionable so that after the mouthguard has been fabricated in the molding apparatus, the user is capable of creating tooth impressions by biting into the material after placing the mouthguard in the mouth. Depending upon the nature of the tooth-impression material that lines the troughs, heating of the mouthguard, such as by placing it in warm water before intra-oral placement, may facilitate the taking of the tooth impressions. The same may be true with an impression tray, which is another form of intra-oral appliance associated with at least one dental arch, embodying principles of the invention. Certain materials, such as EVA for example, may be molded directly onto an underlying layer without the use of adhesive, and remain tooth-impressionable after having been so directly bonded to the underlying layer.

In the case of the lip protector, it is possible to use EVA for both the main body and the liner, with the liner being of lower durometer material. In such an example, the liner can be directly bonded to the main body by injection molding.

Figure 36:
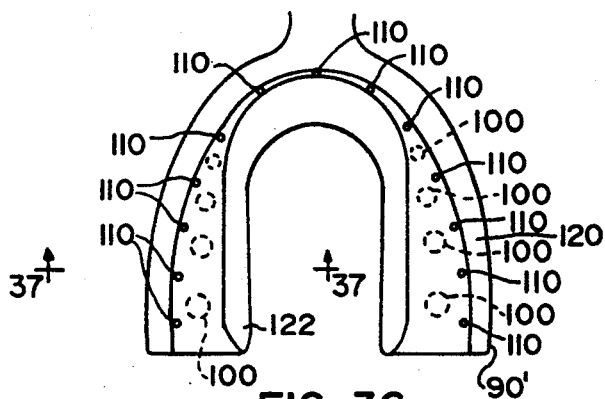
FIG. 36 is a plan view of another embodiment of mouthguard.
Figure 37:
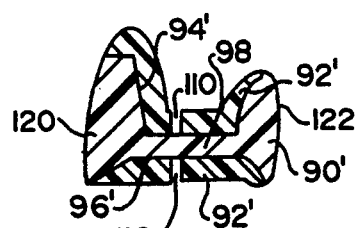
FIG. 37 is a transverse cross sectional view in the direction of arrows 37—37 in FIG. 36.

It is possible to eliminate the resulting holes 110 in the embodiment of FIGS. 36 and 37 without eliminating the use of the stand-off pins. This can be accomplished by making the stand-off pins retractable while the mold remains closed. The pins remain extended for a certain time after the injection, and are then retracted by a timer-controlled mechanism before the flowable material has lost fluency. Upon retraction of the stand-off pins, the still flowable material will flow to fill the holes 110 that would otherwise remain if the pins are allowed to remain extended until the injected material loses fluidity. At the time of their retraction the pressure of the injection has dissipated so that the need for the stand-off pins to hold the main body has passed. It may also be mentioned that stand-off pins could be used to engage the upper and/or lower lips of the buccal wall 120 for the purpose of providing additional support to the main body. Such usage is intended to be additional to the use of pins to support the occlusal wall.

In connection with the break-away attaching strap, it may be noted that the strap 124 of FIG. 40 illustrates three more or less conventional holes. The break-away feature, like that of FIGS. 41 and 42 for instance, may be embodied by creating a furth elongated hole with slits 142 between hole 138 and protuberance 132. Also, the break-away feature of FIG. 45 may be embodied by providing a socket like 156 in the occlusal wall of a main body so that when the barbed end of the strap is inserted, its presence completes the occlusal wall in the region of the socket. Liner material lining the troughs still overlies the top and bottom of such a socket. Such a socket would have a top view like the view of FIG. 45. (As described earlier, the view of FIG. 45 is in the same direction as the view of FIG. 44.)

In the option of using a set of stand-off pins to engage the upper and/or lower edges of the labial wall 120, it should have been noted that those pins may also be retracted by a timer-controlled mechanism to avoid the creation of small holes in the liner material that covers such edges.

While a presently preferred embodiment of the invention has been illustrated and described, it should be appreciated that principles are applicable to other embodiments that are equivalent to the following claims.

What is claimed is:

1. An intra-oral appliance that is associated with a pair of dental arches comprising:
    a first layer comprising a trough for receiving an upper dental arch;
    a second layer in covering relation to said first layer opposite said trough, said second layer being relatively harder than said first layer;
    and a third layer in covering relation to said second layer opposite said first layer, said third layer being relatively harder than said second layer.

2. The improvement set forth in claim 1 in which said second layer is in covering relation to two discrete and separate zones of said first layer.

3. The improvement set forth in claim 1 in which said third layer is in covering relation to only said second layer and not said first layer.

4. The improvement set forth in claim 1 in which said third layer is in covering relation to only said first layer and not said second layer.

5. The improvement set forth in claim 1 in which said third layer is in covering relation to both said first and second layers.

6. An appliance as set forth in claim 1 in which said third layer has a flat surface for engaging teeth of the lower arch, and said third layer is disposed in a trough of said second layer opposite said first layer.

7. An appliance as set forth in claim 1 further including a fourth layer in covering relation to at least a portion of at least one of said first, second, and third layers.

8. The improvement set forth in claim 7 in which said fourth layer is in covering relation to said first, second, and third layers.

9. The improvement set forth in claim 7 in which said fourth layer is in covering relation to only said third layer and not said first or second layers.

10. An intra-oral appliance for association between confronting portions of an upper and lower dental arch comprising:
    a first layer that is toward one of said arches;
    a second layer that is disposed on said first layer toward the other of said arches; and
    a third layer that is disposed on at least one of said first and second layers toward said other of said arches;
    wherein said second layer is relatively harder than said first layer and said third layer is relatively harder than said second layer.

11. An appliance as set forth in claim 10 in which said first layer comprises a trough for receiving the confronting portion of said one of said arches, said second layer has its own trough that is toward the confronting portion of said other of said arches, and said third layer is disposed in said second layer's trough and comprises a flat surface that is toward the confronting portion of said other of said arches.

12. An appliance as set forth in claim 10 further including a fourth layer disposed on at least a portion of at least one of said first, second, and third layers.

* * * * *